(12) United States Patent
Goldberg

(10) Patent No.: US 8,261,748 B1
(45) Date of Patent: Sep. 11, 2012

(54) ORAL DEVICE FOR TREATING SLEEP APNEA

(76) Inventor: Howell Goldberg, Plantation, FL (US)

( * ) Notice: Subject to any disclaimer, the term of this patent is extended or adjusted under 35 U.S.C. 154(b) by 45 days.

(21) Appl. No.: 12/883,156

(22) Filed: Sep. 15, 2010

(51) Int. Cl.
| | |
|---|---|
| A61M 16/00 | (2006.01) |
| A61F 5/37 | (2006.01) |
| A61F 5/56 | (2006.01) |
| A61F 11/00 | (2006.01) |
| A61C 5/14 | (2006.01) |
| A61C 3/00 | (2006.01) |
| A61C 1/08 | (2006.01) |
| A61C 5/00 | (2006.01) |
| A61B 5/117 | (2006.01) |
| A61B 1/32 | (2006.01) |

(52) U.S. Cl. ........ 128/848; 128/846; 128/857; 128/859; 128/860; 128/861; 128/862; 128/200.26; 433/6; 433/7; 433/24; 433/126; 433/136; 433/215; 433/229; 433/898; 433/899; 600/240; 602/902

(58) Field of Classification Search .......... 128/846, 128/848, 857, 859–862, 200.26; 433/6, 7, 433/24, 215, 229, 126, 136, 898, 899; 600/240; 602/902
See application file for complete search history.

(56) References Cited

U.S. PATENT DOCUMENTS

| | | | | |
|---|---|---|---|---|
| 5,649,540 A | * | 7/1997 | Alvarez et al. | 128/848 |
| 6,877,513 B2 | * | 4/2005 | Scarberry et al. | 128/848 |
| 7,607,439 B2 | * | 10/2009 | Li | 128/860 |

* cited by examiner

Primary Examiner — Patricia Bianco
Assistant Examiner — Nihir Patel
(74) Attorney, Agent, or Firm — Glenn E. Gold; H. John Rizvi; Gold & Rizvi, P.A.

(57) ABSTRACT

A device for treating sleep apnea, the device comprising a tongue attachment member and a maxilla attachment subassembly. The tongue attachment member is fabricated having a sheath interlock member extending upward from a dorsal side of a sheath. The sheath is shaped to conform to a surface of an individual's tongue. A tongue receiving cavity is formed within the sheath, the cavity comprising an opening provided at a proximal end for receiving the individual's tongue. The sheath is referenced having a dorsal side and a ventral side. A sheath interlock member extends outward from the dorsal side. The maxilla tray is shaped to conform to and removably engage with an individual's upper dental arch. A tray interlock member extends from an interlock side of the maxilla tray and is positioned to interlock with the sheath interlock member, whereby the system extends an individual's tongue forward to treat sleep apnea.

12 Claims, 7 Drawing Sheets

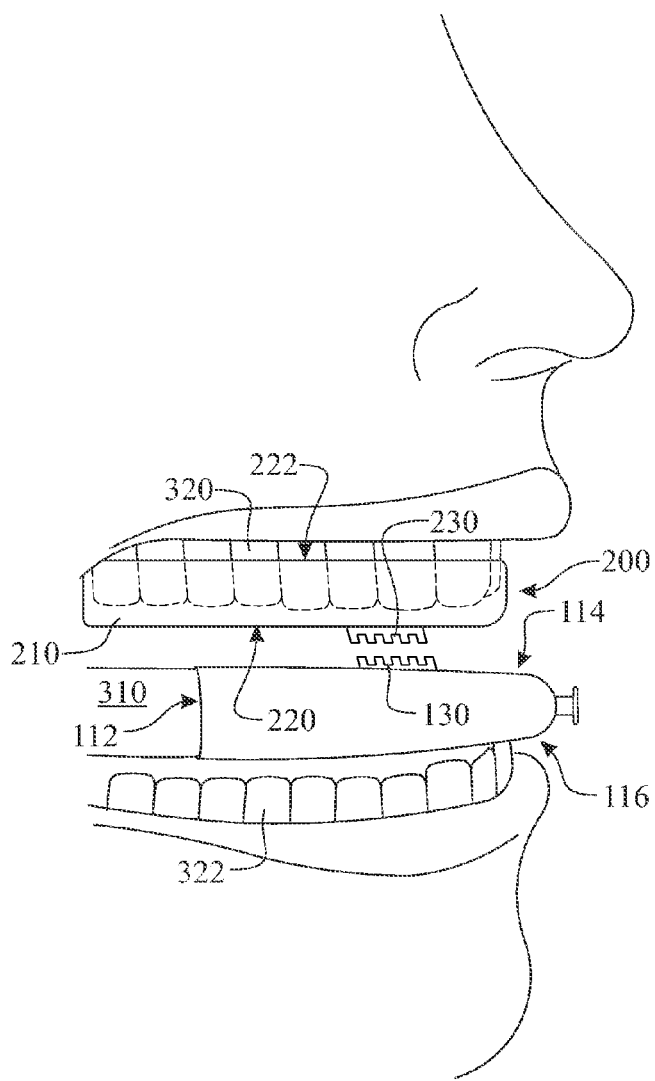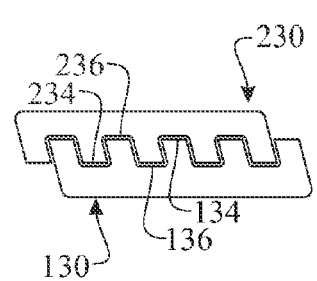
FIG. 12
FIG. 11

ORAL DEVICE FOR TREATING SLEEP APNEA

FIELD OF THE INVENTION

The present disclosure relates to an oral medical apparatus used in the prevention of snoring and sleep apnea. More particularly, it concerns improvements related to comfort and efficiency for its user. Accordingly, this oral medical apparatus improves upon apparatuses that are of similar scope and utility.

BACKGROUND OF THE INVENTION

The present invention provides an oral medical apparatus used in the prevention of snoring and sleep apnea. Snoring is the vibration of respiratory structures and the resulting sound due to obstructed air movement when a human breathes during sleep. Generally, the uvula and soft palate are the anatomical structures that cause the sound of snoring if a human's tongue drops to the back of their mouth during sleep.

Sleep apnea is a sleep disorder characterized by having one or more pauses in breathing, or shallow breaths during sleep, and is typically accompanied by snoring. Each pause or cessation is generally referred to as an apnea, and can last from a few seconds to minutes. Additionally, each apnea may occur from five to thirty or more times per hour of sleep. Although most humans do experience some level of sleep apnea during their lifetime, a relatively smaller percentage (approximately 20%) of humans, suffer with chronic, severe sleep apnea. A combination of factors cause sleep apnea or snoring. One factor is the relaxation of muscle tone that results from sleep. Another factor is the vibration of soft, collapsible tissue surrounding the human airway, which causes snoring.

There are several snoring control devices known in the art. These devices provide for reception of the tongue in a hollow tongue-retained holder. One problem presented by these devices, however, is the inadequate fit between the tongue-retained holder and the user's tongue. In particular, the device determines the position of the tongue. Consequently, a relatively long tongue is not properly or comfortably accommodated within the socket. Different sized devices or custom fabricated devices can be provided to help overcome this shortcoming, wherein the variety and custom fit devices are provided at a higher cost.

Another known device provides a tongue sleeve configured for reception and retention of the outer extent of the user's tongue, and includes a shield shaped to be received and retained outside of the user's lip, as well as a component that allows the user to attach and adjust the shield to the tongue sleeve. This component permits for selective adjustment of the shield's position relative to the tongue, reducing snoring and airway obstruction.

Another device known as the aveoTSD, provides suction between the device and the user's tongue. This suction prevents the tongue from moving toward the back of the mouth, thereby, keeping the airway open during sleep to prevent snoring. The device is known to slip and some wearer's have felt that it is uncomfortable.

Unfortunately, with all of the attempted improvements that have been made in sleep apnea prevention devices, there remains a need for a device that is more comfortable to wear and provides more effective results.

SUMMARY OF THE INVENTION

The present disclosure is generally directed to a sleep apnea control device, the device comprising:

a tongue attachment subassembly comprising:
a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side, and
a sheath interlock member extending outward from the dorsal side of the sheath; and
a maxilla attachment subassembly comprising:
a maxilla tray shaped to conform to and removably engage with an individual's upper dental arch, the maxilla tray defined having an engagement side and an interlock side, and
a tray interlock member extending from the interlock side of the maxilla tray and positioned to interlock with the sheath interlock member, which, when interlocked, extends an individual's tongue during use.

In one aspect, the sheath interlock member is fabricated of a rigid material and the tongue attachment subassembly is fabricated of a pliant material.

In another aspect, the device further includes an air extraction system. An embodiment of the air extraction assembly is provided, which comprises an air extraction valve integrated into the tongue attachment subassembly, wherein the valve is in fluid communication with the tongue receiving cavity. The air extraction device may include an air extraction pipette in fluid communication with an air extraction bulb, where the air extraction pipette is in fluid communication with the air extraction valve to remove air from within the tongue receiving cavity. The air extraction device can be retained or integrated with the air extraction valve or removeable therefrom.

In another aspect, the sheath interlock member further comprises a sheath interlock ridge, and the tray interlock member further comprises a tray interlock ridge, the ridge having an interlock interface to removably engage the sheath interlock ridge and the tray interlock ridge.

In another aspect, the interlock interface is fabricated having a series of teeth and teeth-receiving receptacles.

In another aspect, the interlock teeth are disposed at an acute angle.

In another aspect, the tongue attachment subassembly further includes a tongue base clearance defined by a U-shaped recession in the ventral side, which extends inward from an opening of the tongue receiving cavity opening.

In another aspect, the tongue attachment subassembly is fabricated having a bladder formed within the main body walls, wherein the air extraction valve is provided in fluid communication with the bladder. The user extracts air from the bladder, securing the tongue attachment subassembly to the individual's tongue.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which:

FIG. 11 presents a side elevation view of the apnea control device demonstrating proper positioning within an individual's mouth;

FIG. 12 presents a side elevation view of the tray interlock member engaged with the sheath interlock member;

Like reference numerals refer to like parts throughout the various views of the drawings.

DETAILED DESCRIPTION OF THE INVENTION

Figure 1:
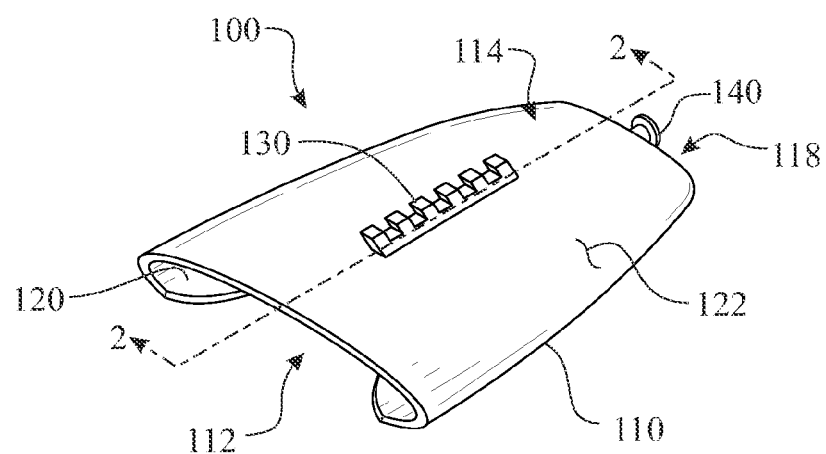
FIG. 1 presents a perspective view of a dorsal side of a tongue attachment member of a sleep apnea control device.
Figure 2:
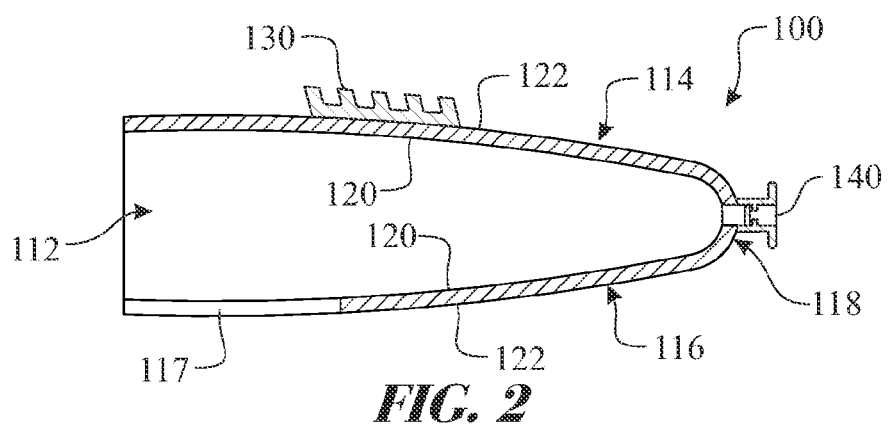
FIG. 2 presents a sectioned view of the tongue attachment member taken along section 2-2 of FIG. 1.
Figure 3:
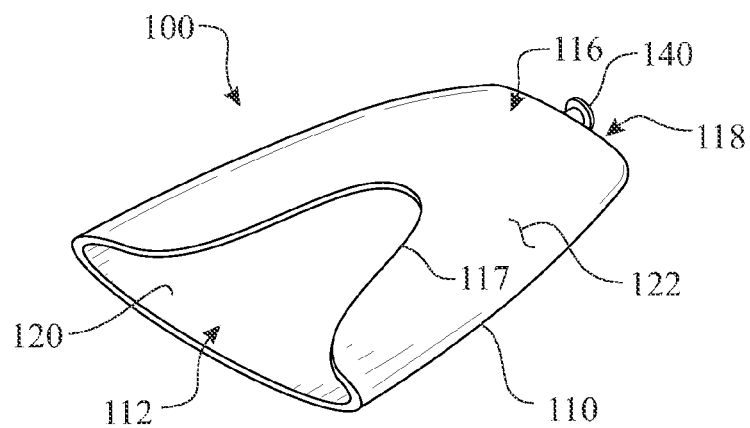
FIG. 3 presents a perspective view of a ventral side of the tongue attachment member.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

A sleep apnea control device is provided for the prevention of snoring and sleep apnea. The sleep apnea control device includes a tongue attachment subassembly 100 and a maxilla attachment subassembly 200, as illustrated in FIG. 11.

Figure 10:
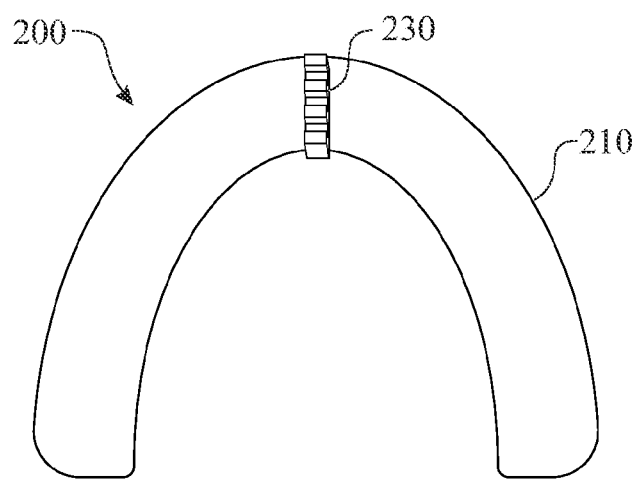
FIG. 10 presents a bottom side plan view of a maxilla attachment member of the apnea control device.

The tongue attachment subassembly 100 is detailed in FIGS. 1 through 9. The maxilla attachment subassembly 200 is detailed in FIG. 10. The tongue attachment subassembly 100 includes a sheath 110, wherein the sheath 110 is defined having a tongue receiving cavity 112 for insertion of an individual's tongue 300. The tongue attachment subassembly 100 can be defined having a dorsal side 114 and a ventral side 116. The sheath 110 can also be defined having an exterior surface 120 and a tongue engagement surface 122. An air extraction valve 140 is integrated into the sheath 110 at a sheath distal end 118. The illustrated air extraction valve 140 is only exemplary and it is understood that it can include any unidirectional valve known by those skilled in the art. The device may be fabricated from any of a plethora of known, non-toxic materials. The sheath 110 is fabricated of a pliant material, such as latex, silicone, rubber, and the like. The sheath 110 can be molded, thermally formed, or constructed using similarly known fabrication techniques.

Figure 7:
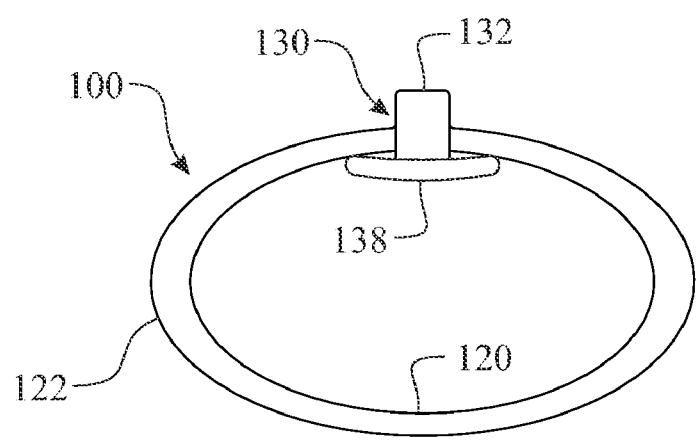
FIG. 7 presents an anterior elevation view of the tongue attachment member.

A sheath interlock member 130 is integrated into a dorsal side 114 portion of the sheath 110. Details of the sheath interlock member 130 are presented in FIG. 6. The sheath interlock member 130 includes an interlock ridge 132 having a series of interlock teeth 134 and interlock teeth-receiving receptacle 136 extending outward from the tongue engagement surface 122 of the dorsal side 114. The preferred design orients the interlock teeth 134 and interlock teeth-receiving receptacle 136 such that a base of each interlock teeth 134 is slightly forward of its top of the respective interlock teeth 134. The sheath interlock member 130 can be integrated into the sheath 110 during the fabrication of the tongue attachment subassembly 100 using the same material, using a different material, or joined in a post fabrication assembly step. The sheath interlock member 130 can include an optional interlock base portion 138 for attachment to the sheath 110. The interlock base portion 138 can be formed having an arched shape with a downward apex, wherein the apex applies additional pressure to the individual's tongue 300. The interlock ridge 132 is inserted through an aperture formed in the dorsal side 114 and attached using any adequate attachment means. An exemplary attachment bonds the interlock base portion 138 to the exterior surface 120 using a bonding media, as illustrated in FIG. 7. The sheath interlock member 130 is preferably constructed from a rigid material, such as plastic, hard rubber, nylon, and the like. The sheath interlock member 130 is preferably fabricated using a molding process, but it is recognized that the sheath interlock member 130 can be fabricated using any reasonable process respective to the material selection. The bonding can be provided using any bonding medium, using a heat staking process, using an ultrasonic welding process, and the like.

Figure 4:
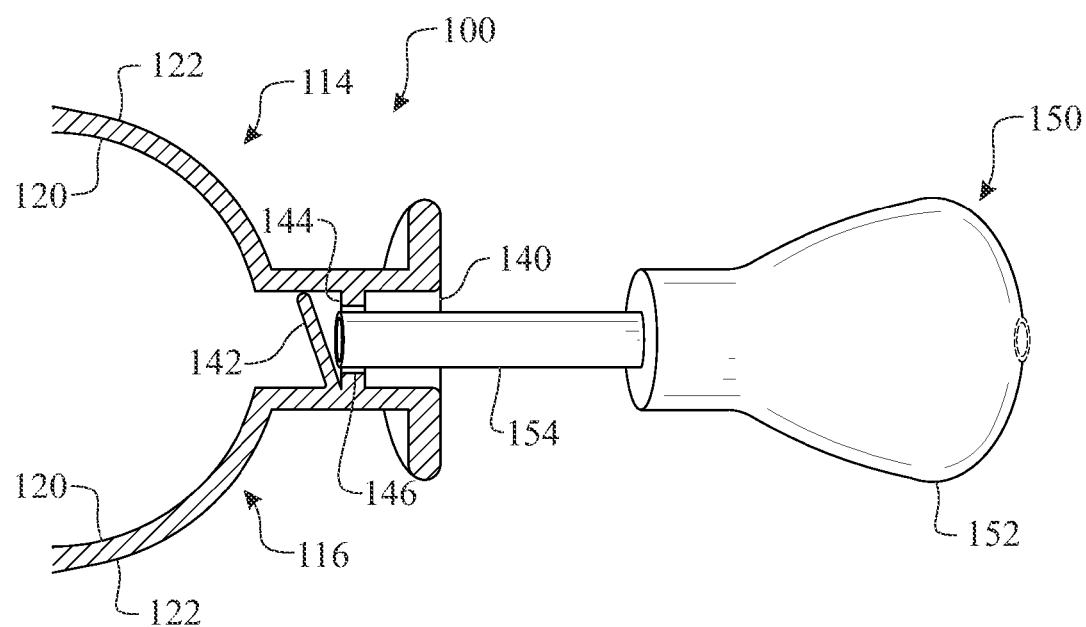
FIG. 4 presents an enlarged sectioned view of a distal end of the tongue attachment member, detailing an air removal system.
Figure 5:
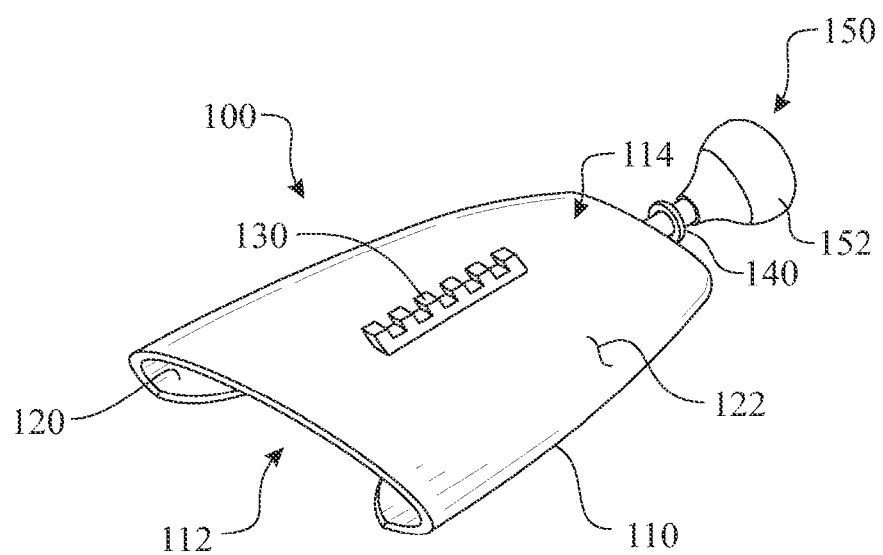
FIG. 5 presents a perspective view of the dorsal side of the tongue attachment member and the air removal system.
Figure 6:
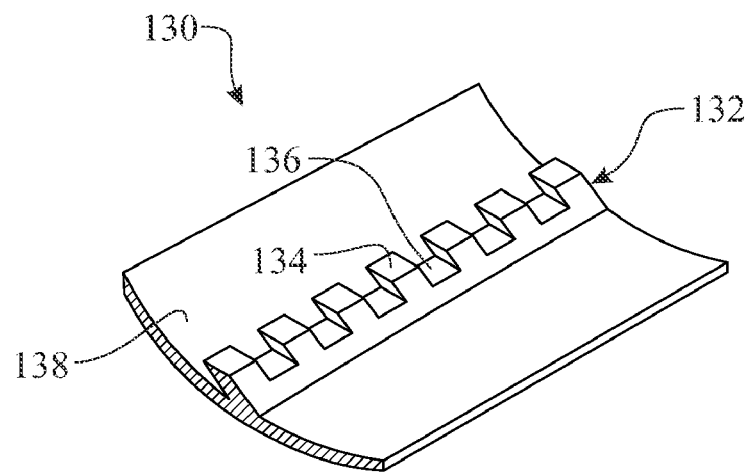
FIG. 6 presents a perspective view of a sheath interlock member.
Figure 8:
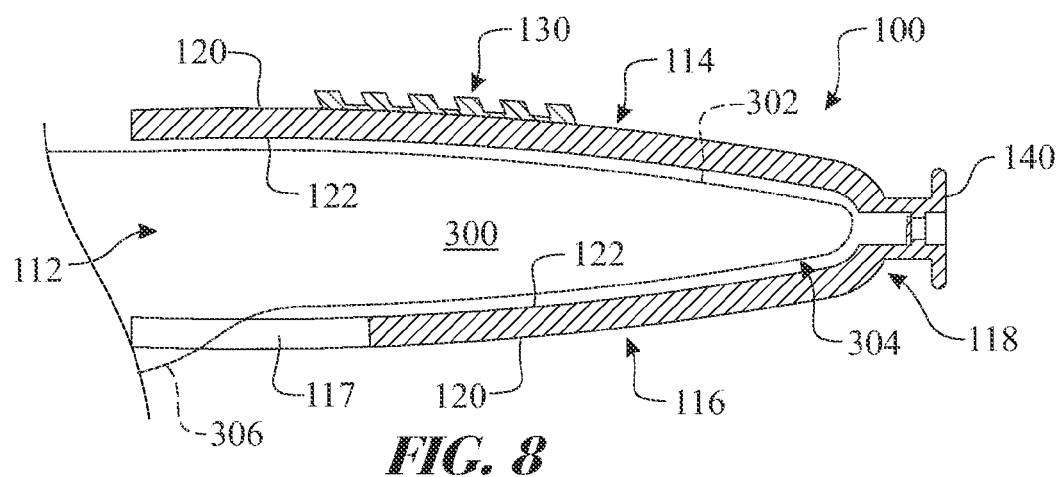
FIG. 8 presents a side sectioned view of the tongue attachment member taken along a longitudinal centerline, wherein the tongue attachment member is secured to an individual's tongue.
Figure 9:
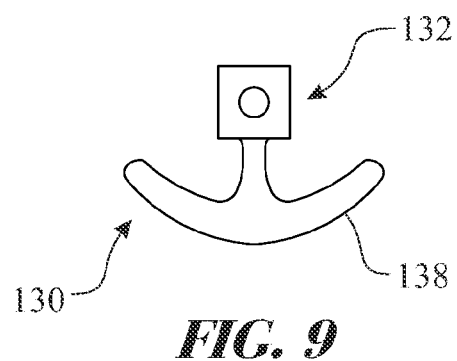
FIG. 9 presents an end elevation view of the sheath interlock member.

The tongue attachment subassembly 100 is placed over and secured to an individual's tongue 300 as illustrated in a FIGS. 8 and 11. A tongue base clearance 117 can be formed within the ventral side 116 of the sheath 110, providing a clearance for a tongue base 306. The tongue base clearance 117 is a recess in the ventral side 116 of the sheath 110, extending inward from an opening for the tongue receiving cavity 112. A securing seal is created by evacuating air from a gap 304 formed between a tongue surface 302 of the individual's tongue 300 and the tongue engagement surface 122. As the sheath 110 is placed upon the individual's tongue 300, air within the tongue receiving cavity 112 is displaced and a seal is created between the tongue surface 302 and a rear portion of sheath 110. A majority of the remaining air is removed using an air removal system. The air removal system includes an air extraction valve 140 and an air extraction device 150. The air extraction device 150 engages with the air extraction valve 140 to extract air from the gap 304. Details of the air removal system are illustrated in FIG. 4. The air extraction device 150 includes an air extraction bulb 152 in fluid communication with an air extraction pipette 154. In the exemplary embodiment, the air extraction pipette 154 is inserted through a unidirectional valve orifice 146 separating a unidirectional valve flap 142 from a unidirectional valve seal 144. This creates an airflow passage between the gap 304 and the air extraction bulb 152. The user would preferably squeeze the air extraction bulb 152 to discharge air from within the air extraction bulb 152 prior to insertion of the air extraction pipette 154 through the unidirectional valve orifice 146. Once inserted, the user would release the pressure from the air extraction bulb 152, thus causing the air extraction bulb 152 to extract air from the gap 304. The user then removes the air extraction device 150 from the air extraction valve 140. The unidirectional valve flap 142 naturally retracts to a sealed configuration, seating against the unidirectional valve seal 144. The removal of air from the gap 304 creates a vacuum, which secures the sheath 110 onto the individual's tongue 300. It is understood that although the illustrations present a removable air extraction device 150, the air extraction device 150 can alternately be integrated into the air extraction valve 140. The air extraction device 150 can be used to aid in the return of air into the air extracted region to aid in removal of the tongue attachment subassembly 100 from the individual's tongue 300.

The maxilla attachment subassembly 200 is formed of a resilient material and shaped to be removably attached to a maxilla (upper jaw) 320. The maxilla attachment subassembly 200 includes a maxilla tray 210, which is formed in a "U-shape", contouring to the maxilla (upper jaw) 320. The maxilla tray 210 is defined having a maxilla tray's attachment side 220 and a maxilla tray's interlock side 222. The maxilla tray's interlock side 222 includes a recession formed into the maxilla tray 210 for receiving individual's teeth. The maxilla attachment subassembly 200 is fabricated having a tray interlock member 230 disposed upon the maxilla tray's interlock side 222 of the maxilla tray 210. The maxilla tray 210 is shaped to be removably attached to the maxilla (upper jaw) 320.

The maxilla tray 210 is secured by its shape and can optionally include one or more features to aid in the engagement with the individual's teeth. The maxilla tray 210 can be formed to mate with the maxilla (upper jaw) 320 by placing the maxilla attachment subassembly 200 into hot water, inserting the maxilla attachment subassembly 200 into the individual's mouth, and placing with finger pressure into an interior recession. This will shape the interior portion of the maxilla tray 210 to mate with the maxilla (upper jaw) 320. Another technique to form the maxilla tray 210 is to have a custom maxilla tray 210 fabricated by the individual's dentist or other oral health care professional. This technique allows the maxilla tray 210 to be custom fit for the user. The custom version of the maxilla attachment subassembly 200 would be fabricated in a manner similar to that for teeth whitening trays from their dentist. A tray interlock member 230 is positioned onto the maxilla tray 210 to interlock with the sheath interlock member 130 as illustrated in FIGS. 11 and 12. An interlock is formed by an engagement between the interlock teeth 134 of the sheath interlock member 130 and the interlock tooth receptacle 236 of the tray interlock member 230, and similarly with the engagement between the interlock tooth 234 of the tray interlock member 230 and the interlock teeth-receiving receptacle 136 of the sheath interlock member 130. The interlock between the sheath interlock member 130 and the tray interlock member 230 draws and maintains the individual's tongue 300 forward, to an extended tongue 310. The teeth engage by the angled relation of the between the interlock tooth 234 and the interlock teeth-receiving receptacle 136. The extended tongue 310 is positioned, resting upon teeth and/or gums of an individual's mandible (lower jaw) 322. The extended tongue 310 and the fixed position of the jaw will reduce or eliminate snoring and sleep apnea.

The sleep apnea control device can be removed from the individual's mouth by opening the individual's mouth, which separates the engaged sheath interlock member 130 and tray interlock member 230, removing the maxilla attachment subassembly 200, then releasing the vacuum holding the tongue attachment subassembly 100 and removing the tongue attachment subassembly 100 from the individual's tongue 300. The vacuum can be removed by squeezing the two sides of the tongue attachment subassembly 100 together to separate the rear edge from the individual's tongue 300 or by inserting the air extraction pipette 154 into the air extraction valve 140, which separates the unidirectional valve flap 142 from the unidirectional valve seal 144, and squeezing the air extraction bulb 152 to inject air into the tongue receiving cavity 112. Upon combining the fixed, forward location 310 of a user's tongue 300 with adequate, uniform suction between the user's tongue 300 and the sheath 310, a comfortable and efficient oral medical apparatus used in the prevention of snoring and sleep apnea is realized.

Although the exemplary embodiments include the air extraction valve 140, it is understood that the tongue attachment subassembly 100 can be fabricated excluding the air extraction valve 140. The user would manually remove the air within the tongue surface 302 by sucking the air therefrom.

Figure 13:
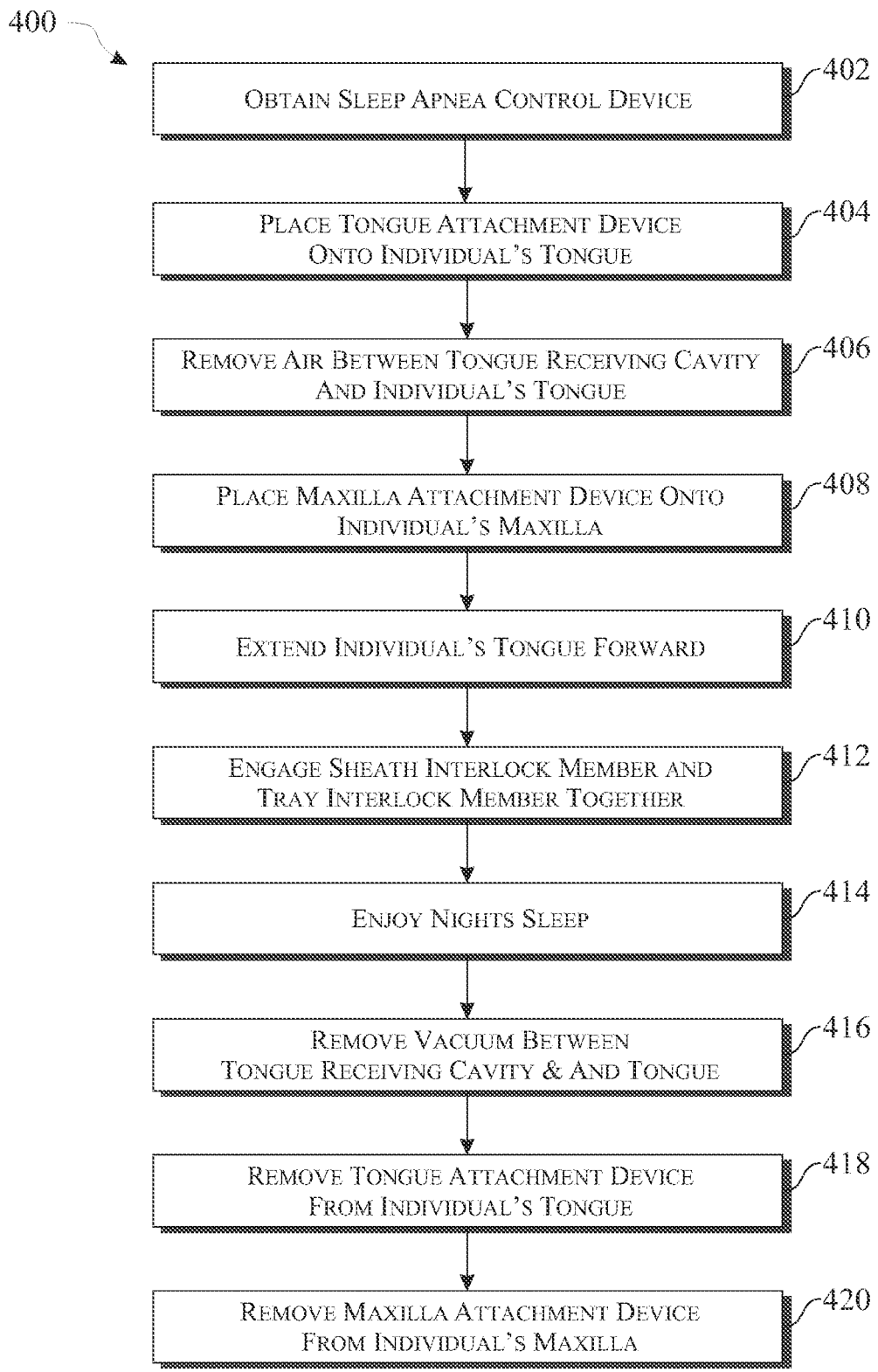
FIG. 13 presents an exemplary flow diagram illustrating a method of use of the sleep apnea control device.

An exemplary sleep apnea control method flow diagram 200 is presented in FIG. 13. The method initiates with a step 402 of the individual obtaining the sleep apnea control device, the device comprising the tongue attachment member 100 and the maxilla attachment subassembly 200. The user places their tongue 300 into the tongue receiving cavity 112 in accordance with a tongue attachment subassembly installation step 404. The user removes a majority of the residual air remaining between the tongue engagement surface 122 of the tongue receiving cavity 112 and the individual's tongue 300 in accordance with an air removal step 406. The maxilla attachment subassembly 200 is positioned, placing the maxilla tray's attachment side 220 against the individual's maxilla (upper jaw) 320 in accordance with a maxilla attachment subassembly installation step 408. The process continues with the user extending their tongue 300 (tongue extending step 410) and engaging the sheath interlock member 130 and the tray interlock member 230 together, referred to as an interlock engagement step 412. At this point, the device is ready for use and the individual can enjoy a night's sleep 414. Upon completion of use, the individual disengages the interlock provided between the sheath interlock member 130 and the tray interlock member 230. The user opens their mouth and removes the vacuum provided between the tongue receiving cavity 112 and the individual's tongue 300 in accordance with a vacuum removal step 416. Once released, the user removes the tongue attachment subassembly 100 from their tongue 300 per a tongue attachment subassembly removal step 418. The use is concluded with the removal of the maxilla attachment subassembly 200 from the individual's maxilla (upper jaw) 320 in accordance with a maxilla attachment subassembly removal step 420. The user then stores the sleep apnea control device for future use.

Figure 14:
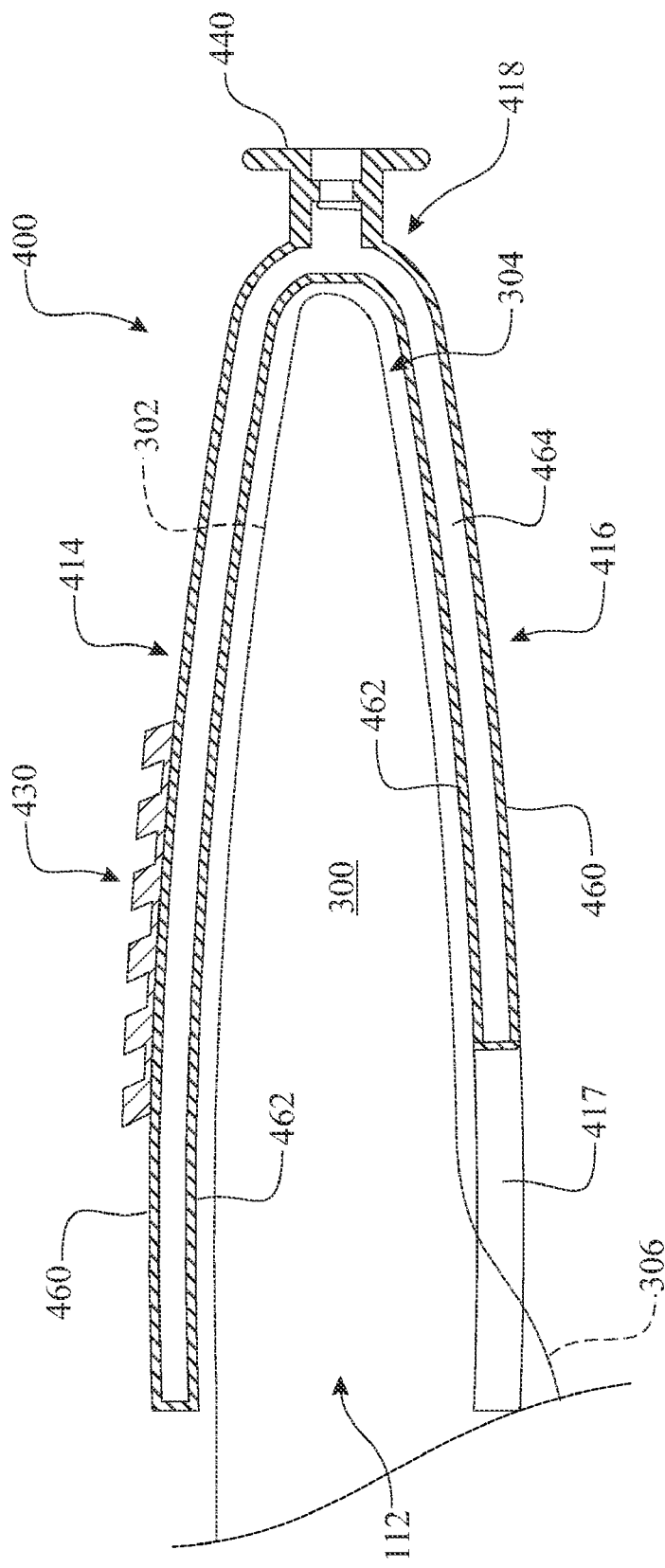
FIG. 14 presents a side sectioned view of an alternate tongue attachment member taken along a longitudinal centerline, wherein the tongue attachment member is secured to an individual's tongue.

An alternate embodiment of the tongue attachment device 100 is presented as a tongue attachment device 400 illustrated in FIG. 14. Like features of tongue attachment device 400 and tongue attachment device 100 are numbered the same except preceded by the numeral '4'. The tongue attachment device 400 utilises an internally provided suction compared to the tongue attachment device 100, which utilises an externally applied suction. The tongue attachment device 400 is fabricated having a bladder air chamber 464 formed therein. The bladder air chamber 464 is defined by a bladder interior wall 462 formed on the tongue-contacting portion of the tongue attachment device 400 and a bladder exterior wall 460 formed on the external portion of the tongue attachment device 400. The user would remove the air from within the bladder air chamber 464 drawing and securing the tongue attachment device 400 onto the individual's tongue 300. The tongue attachment device 400 would be shaped to include a tongue base clearance 117.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A sleep apnea control device, comprising:
   a tongue attachment subassembly comprising:
      a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side,
      a sheath interlock member extending outward from the dorsal side of the sheath, and
   a sheath interlock ridge integrated into the sheath interlock member; and
   a maxilla attachment subassembly comprising:
      a maxilla tray shaped to conform to and removably engage with an individual's upper dental arch, the maxilla tray defined having an engagement side and an interlock side,
      a tray interlock member extending from the interlock side of the maxilla tray and positioned to interlock with the sheath interlock member, which, when interlocked, extends an individual's tongue during use, and
      a tray interlock ridge integrated into the tray interlock member; and
   an interlock interface comprising a series of interlock teeth and interlock teeth receptacles provided between the sheath interlock ridge and the tray interlock ridge.

2. A sleep apnea control device as recited in claim 1, wherein the sheath is fabricated of a pliant material and the sheath interlock member is fabricated of a rigid material.

3. A sleep apnea control device as recited in claim 2, the sheath interlock member further comprising a sheath interlock ridge and an interlock base portion extending generally perpendicularly from a base edge of the sheath interlock ridge; and
   the interlock base portion being attached to the dorsal side of the tongue attachment subassembly.

4. A sleep apnea control device as recited in claim 1, wherein the series of interlock teeth and interlock teeth receptacles are configured at an acute angle.

5. A sleep apnea control device as recited in claim 1, further comprising a tongue base clearance being a U-shaped recession in the dorsal side of the sheath, the clearance extending inward from the opening on the ventral side.

6. A sleep apnea control device, comprising:
   a tongue attachment subassembly comprising:
      a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side,
      a sheath interlock member extending outward from the dorsal side of the sheath;
      a sheath interlock ridge integrated into the sheath interlock member; and
      an air extraction valve integrated into the tongue attachment subassembly, wherein the valve is in fluid communication with the tongue receiving cavity; and
   a maxilla attachment subassembly comprising:
      a maxilla tray shaped to conform to and removably engage with an individual's upper dental arch, the maxilla tray defined having an engagement side and an interlock side, and
      a tray interlock member extending from the interlock side of the maxilla tray and positioned to interlock with the sheath interlock member, which extends an individual's tongue during use;
   a sheath interlock member extending outward from the dorsal side of the tongue attachment subassembly;
      a maxilla attachment subassembly shaped to conform to and removably engage with an individual's upper dental arch, the maxilla attachment subassembly defined having an engagement side and an interlock side; and
      a tray interlock member extending from the interlock side of the maxilla attachment subassembly and positioned to interlock with the sheath interlock member, which, when interlocked, extends an individual's tongue during use, and
      a tray interlock ridge integrated into the tray interlock member; and
   an interlock interface comprising a series of interlock teeth and interlock teeth receptacles provided between the sheath interlock ridge and the tray interlock ridge.

7. A sleep apnea control device as recited in claim 6, wherein the sheath is fabricated of a pliant material and the sheath interlock member is fabricated of a rigid material.

8. A sleep apnea control device as recited in claim 7, further comprising:
   a sheath interlock ridge integrated into the sheath interlock member, the sheath interlock ridge having a base edge and an interlock edge; and
   an interlock base portion extending generally perpendicularly from a base edge of the sheath interlock ridge,
   wherein the interlock base portion is attached to the dorsal side of the tongue attachment subassembly.

9. A sleep apnea control device as recited in claim 6, wherein the series of interlock teeth and interlock teeth receptacles are configured having an acute angle.

10. A sleep apnea control device as recited in claim 6, further comprising a tongue base clearance being a U-shaped recession in the dorsal side of the sheath, the clearance extending inward from the opening on the ventral side.

11. A method of treating sleep apnea, the method comprising the steps of
    obtaining a sleep apnea control device comprising:
       a tongue attachment subassembly comprising:
          a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side, a sheath interlock ridge integrated into the sheath interlock member, an interlock interface provided between the sheath interlock ridge and the tray interlock ridge, and a sheath interlock member extending outward from the dorsal side of the sheath; and a maxilla attachment subassembly comprising:

a maxilla tray shaped to conform to and removably engage with an individual's upper dental arch, the maxilla tray defined having an engagement side and an interlock side, a tray interlock ridge integrated into the tray interlock member, and a tray interlock member extending from the interlock side of the maxilla tray and positioned to interlock with the sheath interlock member, which, when interlocked, extends an individual's tongue during use; and an interlock interface provided between the sheath interlock ridge and the tray interlock ridge;

placing the tongue attachment subassembly onto the individual's tongue by inserting the individual's tongue into the tongue receiving cavity;

removing air between the tongue receiving cavity and the individual's tongue to secure the tongue attachment subassembly in position;

placing the maxilla attachment subassembly onto an individual's maxilla;

extending the individual's tongue forward to align the sheath and the interlock member tray interlock member; and engaging the sheath interlock member and the tray interlock member together;

engaging the sheath and the interlock member tray interlock member together by engaging the interlock interface provided between the sheath interlock ridge and the tray interlock ridge;

utilizing an enhanced sleep apnea control device, which further includes a series of interlock teeth and interlock teeth receptacles formed along an interlock edge of each of the sheath interlock ridge and the tray interlock ridge; and engaging the interlock teeth with the respective interlock teeth receptacles of each of the sheath interlock ridge and the tray interlock ridge.

12. A method of treating sleep apnea as recited in claim 11, the method further comprising the steps of:

utilizing the tongue attachment subassembly further comprising an air extraction valve integrated into the sheath, wherein the valve is in fluid communication with the tongue receiving cavity;

engaging an air extraction device with the air extraction valve; and utilizing the air extraction device to complete the step of removing air between the tongue receiving cavity and the individual's tongue.

* * * * *